United States Patent [19]  [11]  4,159,258
Ohloff et al.  [45]  Jun. 26, 1979

[54] METHOD OF USING NORBORNANE DERIVATIVES IN PERFUME COMPOSITIONS

[75] Inventors: Günther Ohloff, Bernex; Werner Skorianetz, Dardagny, both of Switzerland

[73] Assignee: Firmenich, S.A., Geneva, Switzerland

[21] Appl. No.: 913,476

[22] Filed: Jun. 7, 1978

[30] Foreign Application Priority Data

Jun. 17, 1977 [CH] Switzerland .................. 7449/77

[51] Int. Cl.$^2$ .............................................. C11B 9/00
[52] U.S. Cl. .............................. 252/522; 260/343.21; 252/89 R; 252/174; 424/69; 424/358
[58] Field of Search ................ 252/522; 260/343.2

[56] References Cited
U.S. PATENT DOCUMENTS

| 3,968,070 | 7/1976 | Sundt | 252/522 |
| 3,981,892 | 9/1976 | Skorianetz | 252/522 |
| 4,009,127 | 2/1977 | Ohloff et al. | 252/522 |
| 4,118,343 | 10/1978 | Skorianetz et al. | 252/522 |
| 4,123,394 | 10/1978 | Skorianetz et al. | 252/522 |

FOREIGN PATENT DOCUMENTS 7302539  8/1973  Netherlands .............................. 252/522

OTHER PUBLICATIONS
Synth. Comm., 5, 347, 1975.

*Primary Examiner*—Veronica O'Keefe
*Attorney, Agent, or Firm*—Scully, Scott, Murphy & Presser

[57] ABSTRACT

Tricyclic derivatives of norbornane of formula

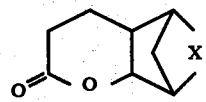

(I a,b,c)

wherein symbol X represents a divalent radical selected from the group consisting of

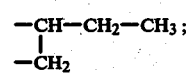 a.

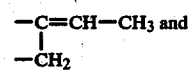

and  b.

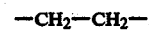

c.

their preparation and their use as perfuming ingredients.

5 Claims, No Drawings

METHOD OF USING NORBORNANE DERIVATIVES IN PERFUME COMPOSITIONS

SUMMARY OF THE INVENTION

The present invention relates to a process for preparing a compound of formula

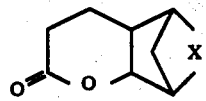
I (b,c)

wherein symbol X represents a divalent radical selected from the group consisting of $$-C\equiv CH-CH_3 \text{ and} \atop -CH_2 \qquad \text{b.}$$

$$-CH_2-CH_2-, \qquad \text{c.}$$

which process comprises the following subsequent steps:

i. reacting acrolein with a compound of formula

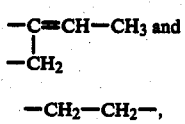
II (b,c)

wherein X represents a divalent radical as defined for formula (Ib,c), to give a compound of formula

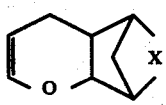 III (b,c)

wherein X represents a divalent radical defined as above, ii. reacting the thus obtained compound with water to give a hydroxy compound of formula

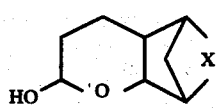
IV (b,c)

wherein X has the above given meaning, and
iii. oxidizing compound IV (b,c).

The invention provides further a process for preparing a compound of formula

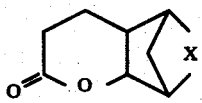
I(a)

wherein X represents a divalent radical of formula $$-CH-CH_2-CH_3 \atop -CH_2 \qquad \text{a.}$$

which comprises steps i. to iii. as defined above and the supplementary step of catalytically hydrogenating compound IV (b), wherein X represents radical $$-C=CH-CH_3 \qquad \text{b.} \atop -CH_2$$

The invention relates moreover to novel compounds I (a) and I (b) which compounds are defined as 3-oxa-9-ethyl-tricyclo[6.2.1.0$^{2,7}$]undecan-4-one,
3-oxa-10-ethyl-tricyclo[6.2.1.0$^{2,7}$]undecan-4-one,
3-oxa-9-ethylidene-tricyclo[6.2.1.0$^{2,7}$]undecan-4-one and
3-oxa-10-ethylidene-tricyclo[6.2.1.0$^{2,7}$]undecan-4-one.

Another object of the present invention relates to a perfuming composition or a perfume base which comprises a fragrance effective amount of a compound of formula I (a,b,c) together with a perfume coingredient, a diluent or an excipient.

Finally, the invention provides a method for improving, enhancing or modifying the odorous properties of perfume compositions or perfume bases, which comprises adding thereto a fragrance effective amount of a compound of formula I (a,b,c).

BACKGROUND OF THE INVENTION

In a constant undertaking towards the replacement of costly natural materials or the reproduction of original fragrance notes, the perfume industry devotes a great deal of efforts to synthesize novel compounds starting from cheaply available raw materials.

Several bi-, tri- and polycyclic derivatives, such as derivatives of decaline, bicyclo[2.2.2]octane, cedrene, caryophyllene and patchoulol for instance, have been proposed as perfuming ingredients in the recent past. Examples of these compounds include the following ones of formula

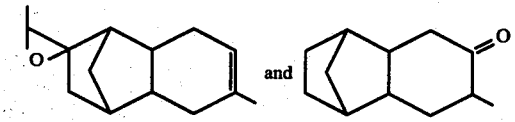

known to develop a floral, woody and spicy odour [see e.g.: Swiss Pat. Nos. 547,850 and 557,870].

We have now discovered that the tricyclic derivatives of norbornane of formula I (a,b,c) possess useful organoleptic properties and that consequently they could be advantageously used in the perfume industry.

Compound of formula I (c), or 3-oxa-tricyclo[6.2.1.0$^{2,7}$]undecan-4-one, has already been disclosed in the scientific literature [see Synth. Comm. 5, 347 (1957)], however its odorous properties have not been described, nor has its possible use as perfume ingredient ever been recognized.

PREFERRED EMBODIMENTS OF THE INVENTION

Compounds I (a,b,c) develop an original odour note which could be defined as very natural, green, fresh, herbacious and slightly fatty or even spicy in some instances. Depending upon the nature of the products to which they are added, compounds I (a,b,c) can develop extremely varied odorous notes, such as green, fruity, aromatic notes, reminiscent in certain instances of tonka beans or medicinal decoctions. The said compounds can consequently be used for the preparation of luxury perfumes as well as perfumed products such as soaps, detergents, cosmetic products or household materials.

In order to achieve the desired effects, compounds I (a,b,c) can be used in proportions comprised in a very wide range of values. These values depend on the nature of the added coingredients as well as on that of the materials to which they are added and on the effects it is desired to achieve. For the preparation of perfume compositions for instance, the most interesting effects are obtained by using amounts of from about 1 to 10% by weight based on the total weight of the finished composition. These quantities are given in a purely exemplificatory manner.

Compounds I (a,b,c) develop also interesting gustative notes ranging from fatty, cuminic and carvone-like notes, reminiscent in certain instances of the taste of coco-nuts. 3-Oxa-tricyclo[6.2.1.0$^{2,7}$]undecan-4-one (compound Ic) presents moreover a slightly fruity and animal character. Consequently, the said compounds can be used for manufacturing artificial flavour compositions and for aromatizing foodstuffs and beverages in general. Typical proportions are in this case of the order of 1 to 100 ppm (parts per million), preferably of about 1 to 5 ppm by weight based on the weight of the flavoured foodstuffs.

In accordance with the process of the invention, the first step for the preparation of compounds I (a,b,c) consists in a Diels-Alder cycloaddition of acrolein on ethylidene-norbornene (or respectively norbornene) according to known techniques [see e.g. H. O. House, Modern Synthetic Reactions, W. A. Benjamin Inc. (1972), p. 817 and ff)]. After mixing, the reactants are brought to a temperature of between about 150° and 250° C. The temperature values vary as a function of the applied pressure; this can vary from about 15 to about 150 atmospheres depending upon the type of vessel employed. The said reaction can be effected in an inert atmosphere, under nitrogen or argon and in the presence of an inhibitor of polymerization, e.g. hydroquinone or pyrogallol.

The following treatment with water can be effected in an inert organic solvent, acetone for instance, and in the presence of a protonic acid, sulphuric acid for example. Temperature is not a determinant factor for obtaining good yields of hydroxy derivatives IV; moderate warming however reduces conveniently the reaction time. Suitable temperatures are of about 50° C. at normal pressure.

According to a variation of the above described steps i. and ii., it was possible to react acrolein with ethylidene norbornene (or respectively norbornene) directly in the presence of water. In such an instance compounds IV (a,b,c) are directly obtained. It has been observed however that the overall yields of thus prepared compounds IV (a,b,c) are not as high as those achieved by carrying out the reaction stepwise by performing steps i. and ii. subsequently.

Oxidation step iii., is effected by means of current oxidation reagents, such as for instance transition metal oxides. Suitable transition metals are chromium, manganese and iron.

The said oxidation can also be carried out by subjecting hydroxy derivative IV (a,b,c) to a catalytic dehydrogenation, preferably by means of chromium salts, such as copper-chromite. The dehydrogenation is effected at elevated temperature, for example at 200°-250° C. and in liquid phase.

The desired compounds of formula I (a,b,c) are then separated by applying conventional techniques; a simple distillation enables to obtain compounds of good purity.

Obtained ethylidene compound IV (b) can then be converted into its saturated derivative of formula IV (a) by conventional catalytic hydrogenation, e.g. in the presence of platinum oxide, palladium on charcoal or Raney-nickel.

The starting materials used in the process of the invention, i.e. acrolein, norbornene and ethylidene norbornene, are commercially available materials.

The compounds obtained in accordance with the invention can occur under the form of mixtures of positional isomers. Their detailed formula is better drawn as follows

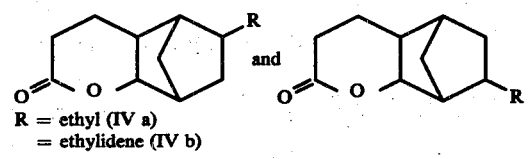

R = ethyl (IV a)
  = ethylidene (IV b)

For economical reasons, these isomeric mixtures are used as directly obtained by the disclosed process without further separation into their constituents.

The invention is better illustrated by the following examples wherein the temperatures are indicated in degrees centigrade.

EXAMPLE 1

3-Oxa-9- and 3-oxa-10-ethylidene-tricyclo[6.2.1.0$^{2,7}$]undecan-4-one a. Two autoclaves have been charged with two fractions, each containing 288 g (2.4 mole) of ethylidene norbornene, 44.8 g (0.8 mole) of acrolein and 1 g of hydroquinone. The reaction is carried out by heating the mixture at 190° for 15 hours. The contents of the two vessels is then combined and fractionally distilled by means of a spinning band column to give a substance at b.p. 45°-55°/0.1 Torr. 150 g of a mixture of 3-oxa-9- and 3-oxa-10-ethylidene-tricyclo[6.2.1.0$^{2,7}$]undec-4-ene were thus obtained. 430 g of starting ethylidene norbornene could be recovered and used for a novel operation.

b. A mixture of 176 g (1 mole) of the obtained mixture of undec-4-ene derivative, 250 g of water, 8 g of concentrated sulphuric acid and 1500 ml of acetone was kept at 55° for 2 hours, whereupon it was diluted with 1000 ml of a saturated NaCl aqueous solution and extracted with 3 fractions of 1000 ml each of ether. The combined organic extracts were subjected to the usual treatments of neutralization, washing and drying over Na$_2$SO$_4$. Subsequent evaporation of the volatile components over NaHCO$_3$ gave a mixture of 3-oxa-4-hydroxy-9- and 3-oxa-4-hydroxy-10-ethylidene-tricyclo[6.2.1.0$^{2,7}$]undecane (186 g; yield 95%).

c. 30 g of the mixture obtained according to letter (b) above were heated under nitrogen at 220° in the presence of 1.5 g of copper chromite. The reaction is over in approximately 2 hours. After cooling and filtration, the mixture was distilled over a short Vigreux column to give 16 g (yield ca. 59% of the desired mixture of 3-oxa- 9- and 3-oxa-10-ethylidene-tricyclo[6.2.1.0$^{2,7}$]undecan-4-one; b.p. 128°–134°/0.1 Torr.

IR: 2930, 1745, 1430, 1335, 1245, 1212, 1165, 1130, 1060, 1025, 982, 943, 818, 709 cm$^{-1}$;

NMR: 1.0–3.0 (14H); 4.2 (1H, m); 5.4 (1H, m) δ ppm

MS: M$^+$=192 (26); m/e=119 (12), 105 (12), 93 (100), 92 (68), 79 (40), 65 (7), 55 (14).

According to a variation of above step (c) the oxidation of 3-oxa-4-hydroxy-9- and 3-oxa-4-hydroxy-10-ethylidene-tricyclo[6.2.1.0$^{2,7}$]undecane was carried out as follows:

1.95 g of said hydroxy-undecane derivative dissolved in 60 ml of CH$_2$Cl$_2$ were stirred for 24 hours at room temperature in the presence of 25 g of MnO$_2$. After filtration, evaporation and fractional distillation there was obtained a fraction having b.p. 150°0.15 Torr consisting of 3-oxa-9- and 3-oxa-10-ethylidene-tricyclo[6.2.1.0$^{2,7}$]undecan-4-one. The product thus obtained was in all respects identical with that obtained sub letter (c) above.

According to another variation of same step (c) the oxidation was effected as follows:

A solution of 7.0 g of CrO$_3$, 10 ml of water and 11.2 g of concentrated H$_2$SO$_4$ was cooled to 0° and added to a solution of the hydroxy derivative obtained sub letter (b) above in 100 ml of acetone. After having been stirred for 2 hours at room temperature, the reaction mixture was diluted with water, neutralized, extracted and finally fractionally distilled to give 13.4 g (yield 71%) of the desired product.

EXAMPLE 2

3-Oxa-tricyclo[6.2.1.0$^{2,7}$]undecan-4-one 56.4 g of norbornene, 16.8 g of acrolein and 0.5 g of hydroquinone were heated 15 hours at 190° in a stainless steel autoclave (pressure about 15 atm.). After evaporation a fractional distillation of the residue gave 22.5 g (yield 49%) of 3-oxa-tricyclo[6.2.1.0$^{2,7}$]undec-4-ene; b.p. 35°–7°/0.5 Torr.

IR: 3060, 2950, 1645, 1460, 1230, 1100, 1060, 970, 930, 910, 730 cm$^{-1}$

NMR: 0.9–2.4 (11H); 3.60 (1H, m); 4.85 (1H, m); 6.30 (1H, m) δ ppm

MS: M$^+$=150 (40); m/e=122 (20), 121 (19), 93 (29), 91 (18), 82 (25), 81 (29), 80 (29), 79 (34), 66 (100), 40 (18), 39 (21).

By oxidation of the obtained product with MnO$_2$ as described above, there was obtained 3-oxa-tricyclo[6.2.1.0$^{2,7}$]undecan-4-one in a 75% yield.

IR: 2950, 2870, 1740, 1460, 1335 - 1325, 1255, 1170, 1140, 1065, 1040, 1000, 965, 940, 775, 715 cm$^{-1}$

NMR: 1.0–2.8 (13H); 4.15 (1H, d, J=5 cps) δ ppm

MS: M$^+$=166 (13); m/e=110 (58), 99 (39), 80 (26), 71 (31), 67 (74), 66 (100), 55 (32), 41 (37).

According to a variation of the above described process, the Diels-Alder addition of acrolein on norbornene can be carried out in the presence of water to yield with a 50% yield 3-oxa-4-hydroxy-tricyclo[6.2.1.0$^{2,7}$]undecane; m.p. 55°–6° (after crystallization in petrol ether).

IR: 3350, 2900, 1450, 1330, 1240, 1200, 1100, 1020, 930, 900, 850 cm$^{-1}$

NMR: 0.8–2.3 (13H); 3.8 (1H, d, J=6 cps) δ ppm

MS: m/e=150 (29), 122 (42), 107 (76), 94 (48), 93 (45), 91 (26), 81 (52), 80 (59), 79 (77), 66 (100), 57 (30), 55 (30), 41 (42), 39 (28).

A subsequent oxidation of the obtained hydroxy derivative (5.8 g) with MnO$_2$ (120 g) in 200 ml of CH$_2$Cl$_2$ gave the desired 3-oxa-tricyclo[6.2.1.0$^{2,7}$]undecan-4-one in a 85% yield.

EXAMPLE 3

3-Oxa-9- and 3-oxa-10-ethyl-tricyclo[6.2.1.0$^{2,7}$]undecan-4-one 3.84 g of the mixture of 3-oxa-9- and 3-oxa-10-ethylidene-tricyclo[6.2.1.0$^{2,7}$]-undecan-4-one obtained in accordance with Example 1 above, in 50 ml of ethanol were subjected to a catalytic hydrogenation in the presence of 3 g of palladium on charcoal at 5%. Filtration, evaporation and distillation enable to obtain 3.7 g (yield 94%) of the title compound having b.p. 160°/0.15 Torr.

IR: 2940, 1745, 1460, 1355, 1332, 1250, 1220, 1162, 1118, 1100, 1058, 1030, 943, 741 cm$^{-1}$

NMR: 0.8–2.6 (17H); 4.1 (1H, m) δ ppm

MS: M$^+$=194 (9), m/e=165 (7), 138 (13), 121 (13), 109 (15), 95 (75), 94 (100), 79 (25), 67 (35), 55 (31), 41 (35).

EXAMPLE 4

A base perfuming composition was obtained by admixing the following ingredients (parts by weight):

| | |
|---|---|
| Benzyl salicylate | 200 |
| Phenylpropanol | 100 |
| Hydratropic alcohol | 80 |
| Brazil rose wood oil | 60 |
| Methyl-nonyl-acetaldehyde 10%* | 60 |
| Terpineol | 60 |
| p-t-Butyl-Cyclohexyl acetate | 50 |
| Lavandin oil | 50 |
| Galbanum oil 10%* | 50 |
| α-Ionone | 40 |
| Cyclopentadecanolide 10%* | 40 |
| Pine balsam absolute 10%* | 30 |
| Hydroxy-citronellal | 20 |
| 1,1-Dimethyl-6-t-butyl-4-acetyl-indane | 10 |
| Oak moss concrete 50%* | 20 |
| Trimethyl-hexanal 10%* | 20 |
| α-Damascone 10%* | 10 |
| β-Damascone 10%* | 5 |
| Ethyl acetyl-acetate | 5 |
| Isobornyl acetate | 20 |
| Diethyl phthalate | 20 |
| | 950 |

*in diethyl phthalate

The above base possesses a pleasant odour of herbaceous type and is particularly suitable to perfume shampoos or capillary lotions.

By adding to 95 g of the above base 5 g of the compounds obtained according to Example 1 above, there was obtained a novel perfuming composition whose fragrance was fresher, more harmonious and possessed more lifting than the base composition. The novel composition possessed moreover a more distinct character.

By adding, in the same proportions, the title compound obtained according to Example 3 above to the base composition, an analogous effect was observed.

The addition of 5 g of 3-oxa-tricyclo[6.2.1.0$^{2,7}$]undecan-4-one to 95 g of the base composition enabled to obtain a novel composition whose herbal character was enhanced. The novel composition possessed moreover a slightly fruity character.

EXAMPLE 5

The compound obtained according to Example 1 above was used to perfume several technical commercial articles, namely those defined in the following table.

TABLE

| article | concentration (weight %) | |
| --- | --- | --- |
| Eau de toilette | 5 | |
| Toilet soap | 1 | |
| Talc | 1 | |
| Deodorizer | 0.4 | (of total volume, propellant inclusive) |
| Antiperspirant | 0.5 | " |
| Night beauty cream | 0.4 | |
| Day beauty cream | 0.4 | |
| Hair lacquer | 0.4 | (of total volume, propellant inclusive) |

The perfume developed in all the above given media was fresh, pleasant and possessed a herbaceous character, moreover it proved remarkably stable over a prolonged period even at moderate temperature (40° C.).

What we claimed is:

1. Method for improving, enhancing or modifying the odorous properties of perfume compositions or perfume bases, which comprises adding thereto a fragrance effective amount of a compound of formula

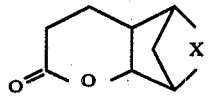

wherein symbol x represents a divalent radical selected from the Group consisting of

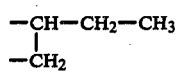 a.

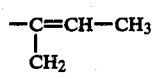 b.

 c.

2. The method of claim 1 wherein such compound is 3-Oxa-9-ethyl-tricyclo[6.2.1.0$^{2,7}$]undecan-4-one.

3. The method of claim 1 wherein such compound is 3-Oxa-10-ethyl-tricyclo[6.2.1.0$^{2,7}$]undecan-4-one.

4. The method of claim 1 wherein such compound is 3-Oxa-9-ethylidene-tricyclo[6.2.1.0$^{2,7}$]undecan-4-one.

5. The method of claim 1 wherein such compound is 3-Oxa-10-ethylidene-tricyclo[6.2.1.0$^{2,7}$]undecan-4-one.

* * * * *